United States Patent [19]
Melanson et al.

[11] Patent Number: 5,677,190
[45] Date of Patent: Oct. 14, 1997

[54] CELL AND CIRCUIT FOR MONITORING PHOTOCHEMICAL REACTIONS

[75] Inventors: Paul C. Melanson; Robert L. Garvin; Lawrence K. de Martin, all of Boulder; David A. Pane, Lyons; James A. Valdez, Boulder, all of Colo.

[73] Assignee: Anatel Corporation, Boulder, Colo.

[21] Appl. No.: 355,968

[22] Filed: Dec. 14, 1994

[51] Int. Cl.$^6$ ............................................. G01N 21/00
[52] U.S. Cl. ............................. 436/141; 422/78; 422/79; 422/80; 422/82.02; 422/82.12; 436/133; 436/150; 436/159; 436/162; 65/38; 65/42; 65/43; 65/59.1; 65/59.21; 65/59.22; 65/59.23; 65/59.24; 65/59.25; 65/59.26; 65/59.27; 65/59.28
[58] Field of Search ...................... 422/78, 79, 80, 422/82.02, 82.12; 436/162, 133, 146, 150, 159; 65/38, 42, 43, 59.1, 59.2, 59.21, 59.22, 59.23, 59.24, 59.25, 59.26, 59.27, 59.28

[56] References Cited

U.S. PATENT DOCUMENTS

| | | | |
|---|---|---|---|
| 2,019,871 | 11/1935 | Pettingill et al. | 23/230 |
| 3,224,837 | 12/1965 | Moyat | 23/230 |
| 3,287,088 | 11/1966 | Seevers | 23/230 |
| 3,470,465 | 9/1969 | Wuschke | 324/65 |
| 3,535,087 | 10/1970 | Hart et al. | 23/253 |
| 3,607,071 | 9/1971 | Staffin et al. | 23/230 PC |
| 3,738,812 | 6/1973 | Berry et al. | 23/253 R |
| 3,854,877 | 12/1974 | Csaky et al. | 23/230 PC |
| 3,906,353 | 9/1975 | Murdock | 324/30 R |
| 3,955,924 | 5/1976 | Northmore et al. | 23/230 PC |
| 3,958,941 | 5/1976 | Regan | 23/253 PC |
| 3,964,868 | 6/1976 | DiCola et al. | 23/253 PC |
| 4,140,018 | 2/1979 | Maldarelli et al. | 73/423 B |
| 4,227,151 | 10/1980 | Ellis et al. | 324/448 |
| 4,248,598 | 2/1981 | Blunck | 23/230 M |

(List continued on next page.)

FOREIGN PATENT DOCUMENTS

| | | |
|---|---|---|
| 0135685 | 2/1984 | European Pat. Off. |
| 0234875 | 2/1987 | European Pat. Off. |
| 0288099 | 10/1988 | European Pat. Off. |
| 0459782 | 4/1991 | European Pat. Off. |
| 0498888 | 8/1992 | European Pat. Off. |
| 2581196 | 4/1985 | France. |
| 3117537 | 4/1981 | Germany. |
| 3223167 | 6/1982 | Germany. |
| 2029015 | 3/1980 | United Kingdom. |
| 9113362 | 9/1991 | WIPO. |
| 9218856 | 10/1992 | WIPO. |

OTHER PUBLICATIONS

Skalar, "Dissolved/Total . . . ", product description Jun. 1993, cat.311. 5p.
"The Application of On–Line . . . ", Poirier et al, *Ultrapure Water*, Jul./Aug., 1986, pp. 19–26.
"Conductometric Sensor . . . ", J.J. Symanski, *Anal. Chem.*, 1983, 55, 1152.
"A New Approach . . . ", Poirier et al, *American Laboratory*, Dec. 1978.

*Primary Examiner*—Jill Warden
*Assistant Examiner*—Sharidan Carrillo
*Attorney, Agent, or Firm*—Michael de Angeli

[57] ABSTRACT

An improved measurement cell and circuit for measuring the electrical characteristics of a liquid sample during exposure to radiation includes a glass cell formed of a main tube extending generally parallel to an elongated lamp emitting the radiation, and a pair of electrodes disposed axially within the sample tube. In the preferred embodiment, the ends of the cell are formed of glass twinbore tubing fused to the glass main tube, the bores retaining ends of the electrodes. Inlet and outlet tubes and a temperature sensing well may also be fused to the main tube. In an implementation for measurement of TOC in water by oxidation to $CO_2$, the source comprises a low pressure mercury vapor lamp, and the electrodes are formed of solid Ti with catalytic $TiO_2$ surfaces. The circuit used to monitor variation in electrical characteristics of the liquid during UV exposure controls flow of power to op-amps in order to multiplex a drive signal between the UV exposure cell, a calibration resistor, and a temperature sensor.

39 Claims, 4 Drawing Sheets

U.S. PATENT DOCUMENTS

| | | | |
|---|---|---|---|
| 4,272,679 | 6/1981 | Blades | 422/146 |
| 4,277,438 | 7/1981 | Ejzak | 422/80 |
| 4,288,229 | 9/1981 | Mar | 23/230 PC |
| 4,293,522 | 10/1981 | Winkler | 422/80 |
| 4,304,996 | 12/1981 | Blades | 250/373 |
| 4,357,668 | 11/1982 | Schwartz et al. | 364/497 |
| 4,383,221 | 5/1983 | Morey et al. | 324/439 |
| 4,418,566 | 12/1983 | Beck et al. | 73/23 |
| 4,626,413 | 12/1986 | Blades et al. | 422/78 |
| 4,627,921 | 12/1986 | Meyers et al. | 210/668 |
| 4,666,860 | 5/1987 | Blades et al. | 436/146 |
| 4,683,435 | 7/1987 | Blades | 324/442 |
| 4,749,657 | 6/1988 | Takahashi et al. | 436/146 |
| 4,825,168 | 4/1989 | Ogawa et al. | 324/439 |
| 4,851,130 | 7/1989 | May | 210/750 |
| 4,868,127 | 9/1989 | Blades et al. | 436/146 |
| 5,047,212 | 9/1991 | Blades et al. | 422/82.02 |
| 5,260,663 | 11/1993 | Blades | 344/442 |
| 5,272,091 | 12/1993 | Egozy et al. | 436/146 |
| 5,275,957 | 1/1994 | Blades et al. | 436/133 |
| 5,334,940 | 8/1994 | Blades | 324/442 |
| 5,395,522 | 3/1995 | Malanson et al. | 210/202 |
| 5,518,608 | 5/1996 | Chubachi | 210/96.1 |

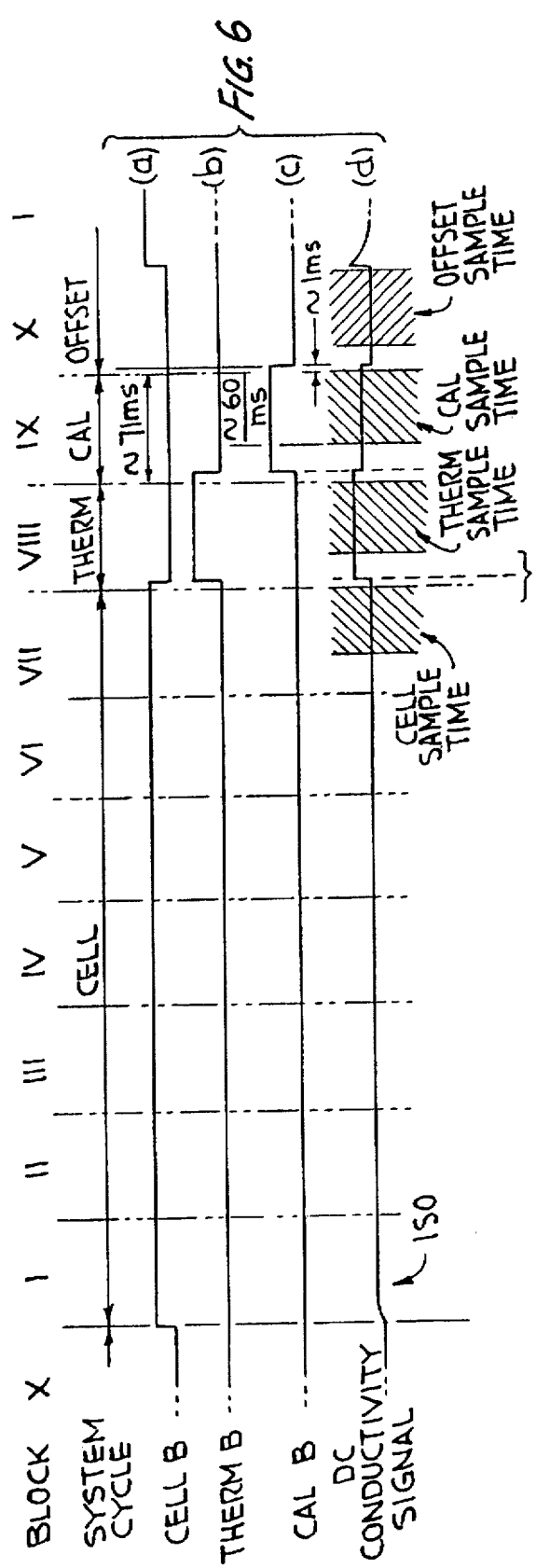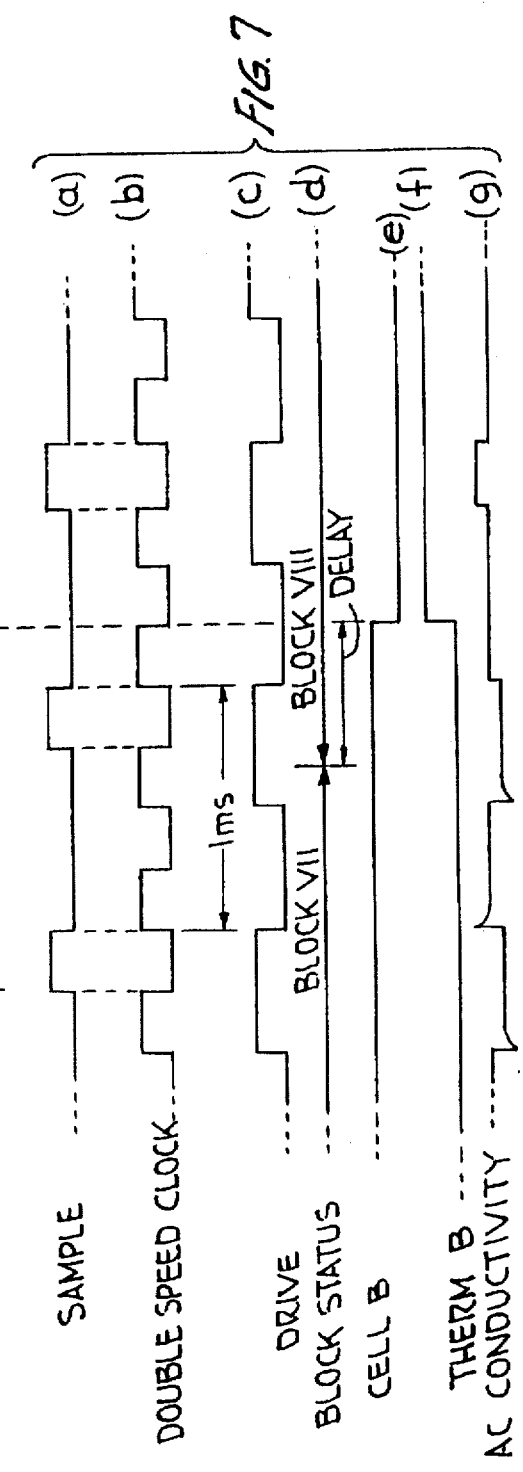

CELL AND CIRCUIT FOR MONITORING PHOTOCHEMICAL REACTIONS

FIELD OF THE INVENTION

This invention relates generally to the field of monitoring photochemical reactions, for example, wherein radiation of predetermined wavelength irradiates a liquid sample to initiate or accelerate a reaction therein, while the conductivity or another electrical characteristic of the liquid is measured to monitor progress of the reaction. In a particular embodiment, the invention relates to measuring the total organic carbon content of water.

BACKGROUND OF THE INVENTION

The assignee of the present application possesses a number of patents directed to instruments for measurement of the total organic carbon content ("TOC") of water. The instruments disclosed in these patents operate primarily by exposing a sample of water containing organic contaminants to ultraviolet radiation ("UV"), while measuring the change in the electrical conductivity of the sample due to the formation of carbon dioxide by oxidation of the organics. U.S. Pat. Nos. directed to such instruments include 4,626,413, 4,666, 860, and 5,047,212. The further discovery that certain materials when exposed to UV serve as UV-stimulated catalysts, speeding and promoting the oxidation of the organics to carbon dioxide, is reflected in U.S. Pat. Nos. 4,868,127 and 5,275,957. Circuits employed in such instruments for measuring the conductivity of water samples in a cell during exposure to UV are disclosed in U.S. Pat. Nos. 4,683,435, 5,260,663, and 5,334,940.

As typically implemented, the instruments for measuring the total organic carbon content of water disclosed in the patents listed above comprise a sample cell wherein a static sample of water is maintained between conductivity-measuring electrodes while the sample and the electrodes are exposed to a source emitting UV of 184 and 253 nanometers wavelength. Preferably, the electrodes are formed of solid titanium oxidized so as to possess a $TiO_2$ surface; this N-type semiconductor material catalyzes the reaction of organic carbon compounds in water to $CO_2$ when exposed to short wavelength UV.

It is generally significant to the operation of such instruments that the water being analyzed be what is normally termed in the art "high purity" or "ultrapure" water, typically, water having been deionized so as to have a very low conductivity, e.g., 1–18 Mohm-cm. Only when the water is deionized will the carbon dioxide formed by oxidation of the organics be dissociated as ions in solution, such that monitoring the conductivity of the sample is effective to evaluate its $CO_2$ content. By comparison, if the conductivity of the sample is relatively high, that is, if the water sample is not ultrapure, a fraction of the $CO_2$ forms gas bubbles; the amount of $CO_2$ in solution, and thus the conductivity of the water, depends on the water's pH, bicarbonate, and carbonate levels. These variables cannot be readily measured and depend in turn on the water's chemistry in a complex manner. The result is that measurements of the conductivity of samples of water that are not deionized cannot be readily converted to values for the $CO_2$ content thereof.

As detailed further in U.S. Pat. Nos. 5,260,663 and 5,334,940, accurately measuring the conductivity of a water sample, e.g., to monitor changes therein to determine the organic carbon content of the water, is not a simple matter. In effect, both series and parallel capacitances are present in the sample cell; if not properly compensated for, erroneous measurements of conductivity will be made. Further, the UV incident on the electrodes induces a voltage thereacross according to the photoelectric effect. These patents disclose several improvements in circuits accurately compensating the measurements of conductivity for such inherent capacitance and other sources of error.

While the instruments described in the above-mentioned patents of the assignee have been highly successful, and have in fact captured a very substantial fraction of the world market for instruments of their type, there is always room for improvement, particularly with respect to lowering the cost of the product. A particular goal has been the simplification of the cell design shown in, for example, U.S. Pat. No. 5,279,957, which includes several costly machined titanium components. Further, it was desired to simplify the circuit shown in U.S. Pat. Nos. 5,260,663 and 5,334,940, in particular, to reduce the number of field effect transistor switching elements, which introduce series resistances that require complex compensation techniques.

In addition to the commonly assigned patents mentioned above, additional prior art germane to the subject of analyzing total organic carbon ("TOC") in water includes U.S. Pat. No. 3,958,941 to Regan, Hüls AG German published patent application 3,223,167, and U.S. Pat. No. 5,272,091 to Egozy et al.

The Regan patent shows a system for analyzing TOC in non-ultrapure waters, wherein a substantial fraction of the $CO_2$ formed upon oxidation of the organics by exposure to UV remains in gaseous form. Accordingly, in the Regan patent, the $CO_2$ is removed from the sample by bubbling air through the sample; the $CO_2$-bearing air stream is then introduced into a stream of ultrapure water, in which the $CO_2$ dissociates, becoming ionic. The conductivity of the ultrapure water is measured to evaluate the $CO_2$ content. It will be apparent that such a system is rather complex, and that the $CO_2$ transport step cannot be carried out with complete repeatability. Accordingly, the Regan instrument is of limited accuracy and is suited only for non-ultrapure water systems.

The Hüls AG patent teaches an instrument measuring TOC in waters of a wide variety of conductivity. The basic measurement technique used in connection with ultrapure water is to measure the conductivity of a flowing stream prior to and after exposure to UV, such that the change in conductivity provides a measure of organics therein. However, because the rate of oxidation of various organics differs very greatly, at best the Hüls instrument can provide a qualitative indication of the amount of organics present and cannot be relied upon to provide an accurate measurement thereof; since organics in the sample are not oxidized to completion, various types of organics will effectively be measured in greater or lesser proportions depending on the oxidisability of the particular organics present, the average residence time of the sample in the UV exposure cell, the effective UV intensity, and other variables.

The instruments disclosed in the commonly-assigned patents discussed above typically address this problem by retaining a static sample in the UV exposure chamber and monitoring the sample's conductivity continuously as a function of time to determine when the reaction is substantially completed, such that the TOC can then be accurately measured. Where a series of generally similar samples are taken, such that the conductivity of each varies generally similarly with time, the final conductivity can be inferred accurately before the oxidation is complete. Furthermore, under certain circumstances two such instruments connected in series can be used to detect changes in the conductivity of a sample stream responsive to partial oxidation due to UV irradiation, e.g., in monitoring a continuous process. See the discussion at columns 21-22 of patent 4,666,860.

More recently, there has been issued the Egozy et al patent. Generally similar to the Hüls AG patent, Egozy teaches measuring the conductivity of ultrapure water on inlet and outlet sides of a UV exposure chamber for monitoring the TOC of a continuous process stream. Egozy acknowledges that accurate measurement of the TOC of the stream requires a sample to be oxidized to completion, or, at minimum, that the oxidation must progress sufficiently with respect to a single sample that its ultimate conductivity can be predicted. As noted, predicting the final TOC after partial oxidation of a particular sample is also suggested in various of the commonly-assigned patents discussed above.

Also generally relevant is UK Patent Application 2,029, 015 to Loeliger. This disclosure relates to measuring the oxidisability of food products by exposing such products to UV. The oxygen consumed is measured using a polarographic electrode.

While as indicated above, the present invention is directed primarily to improvements in instruments, measurement techniques, and circuits for the measurement of the total organic carbon content of ultrapure water, in fact there are additional applications for the teachings of the invention. Essentially the present invention provides an improved, highly efficient, and very low-cost cell and circuit for monitoring the conductivity (or another electrical characteristic, such as impedance or inductance) of a liquid sample while exposing the sample to radiation of a predetermined frequency. This cell may find use in flow injection analysis, monitoring of organic digestion, nitrogen-containing compound analysis, or other elemental analysis, and liquid chromatography. The circuits disclosed herein also have applicability beyond analysis of liquid samples during irradiation.

OBJECTS AND SUMMARY OF THE INVENTION

It is therefore an object of the invention to provide an improved, in particular, a less expensive cell for monitoring the conductivity or another electrical characteristic of a liquid therein during exposure to radiation of a predetermined wavelength.

It is a further object of the invention to provide such a cell wherein the electrodes used to monitor the conductivity of the liquid have surfaces of a material photocatalytically stimulating the reaction of interest when exposed to radiation from the source, and wherein the surfaces of the electrodes are accordingly exposed substantially directly to radiation from the source.

It is a further object of the invention to provide a low-cost circuit for measuring the electrical characteristics of a given object, such as the conductivity of a liquid sample in a cell during exposure to radiation, compensating accurately for spurious capacitance and other effects, and useful over a wide range of conductivity values.

It is a further and more specific object of the invention to provide an improved apparatus, circuit, and method for measurement of the total organic carbon content of a sample of water which may be implemented relatively inexpensively while providing highly reliable and accurate measurement.

These and other objects of the invention which will appear as the discussion below proceeds are satisfied by a cell comprising a central section of tubing of a material transparent to the radiation of interest, and having a pair of parallel electrodes mounted such that they extend axially along the length of the tube. In use, this cell is placed in juxtaposition to an elongated source of radiation of predetermined frequency, such that a liquid sample in the tube is exposed to the radiation while the electrodes are employed to measure the conductivity of the liquid. In the context of a cell optimized for measuring the TOC of an high purity water ("HPW") sample, the source emits ultraviolet radiation of 184 and 253 nm wavelengths; preferably the electrodes are solid Ti rods having a $TiO_2$ coating formed thereon by oxidation. The $TiO_2$ surfaces are exposed directly to the UV radiation, and catalyze the oxidation of organics in the water to $CO_2$.

In a particularly convenient embodiment, the ends of the cell are formed of short sections of quartz twinbore tubing, sized such that the Ti rods fit snugly within the bores of the twinbore tubing, and fused to the main tube, providing a secure and relatively inexpensive mounting structure for the electrodes. Inlet and outlet tubes are similarly fused into the main portion of the cell, allowing sample entry and exit. A temperature sensor well is similarly fused to the main body of the tube, such that a thermistor or other temperature sensor disposed therein is in good thermal communication with the sample, but is not in fluid communication therewith.

In order to limit the effects of UV on the components of the system, the inlet and outlet tubes, the end members, and the sensor well are all made of UV-absorptive glass or quartz, while the main body of the tube, as mentioned, is formed of a UV-transparent material. At the base of the temperature sensor well, where the UV-transparent main tube forms the base of the well, a coating of a UV-absorptive, thermally conductive metal may be provided, such as copper, aluminum, or gold.

Electrical connections to the electrodes may be made by extending distal ends thereof beyond one of the end members formed of twinbore tubing, and a mechanical, adhesive, or metal/glass seal provided. In a successfully tested embodiment, an elastomeric seal is compressed into the twinbore tubing by a mechanical fastener. Both are protected by UV-opaque materials to prevent deterioration over time.

In a complete instrument, a UV source comprising a conventional low pressure mercury vapor lamp is mounted in a sealed housing together with the cell. The presence of stray oxygen or oxygen entering through leaks in the seal is addressed by providing a quantity of a material which preferentially reacts with ozone created when short wavelength UV irradiates oxygen in the air, such as activated charcoal or aluminum, in the chamber housing the UV lamp. In this way, both oxygen and ozone are prevented from absorbing the UV, which would reduce the efficiency of the instrument.

As indicated above, the principal design goals of the conductivity circuit according to the present invention are to reduce the cost of the componentry necessary to provide an accurate value for the conductivity of a solution of a liquid sample, such as ultrapure water, during a photochemical reaction, such as oxidation of organic material in water to $CO_2$. As in the case of the prior U.S. Pat. Nos. 4,683,435, 5,260,663 and 5,334,940, an AC square wave drive signal is capacitively coupled to the conductivity cell; according to the invention, the same drive signal is successively applied to the thermistor and to a gain calibration resistor. This multiplexing of the input signal is accomplished by supplying the drive signal to a set of op-amps, one each in series with the cell, the thermistor, and the calibration resistor; the op-amps conduct the drive signal to the corresponding load only when power is applied thereto, controlled by paired switching transistors responsive to sequences of control signals provided by a microprocessor.

A further op-amp configured as a transimpedance receiver converts the resulting AC current into a voltage waveform. This AC voltage is repeatedly sampled synchronously in order to rectify the signal and to reject series and parallel cell capacitance. The resulting DC signal is filtered and converted to a digital signal; in a preferred embodiment, this is done by converting the DC signal to frequency and measuring the frequency. The microprocessor then analyzes the signal proportional to the conductivity of the solution to determine the TOC thereof, generally in accordance with teachings of the prior commonly-assigned patents referred to above.

Thus, an AC-coupled multiplexer connects the input drive signal successively between the conductivity cell, a thermistor used for temperature correction of the conductivity measurement, and a calibration resistor. The input signal is also not connected for a period, during which an offset measurement is made. The multiplexer consists of three voltage follower op-amps with switched power supply connections. The connection sequence for the op-amps is maintained such that each has a maximum off-time and a minimum on-time varying with the conductance range for each input to maintain accuracy. Power switching is performed in a consistent cycle synchronous to the conductivity drive signal, to maintain the proper charge on input and output coupling capacitors provided for each op-amp to eliminate DC current flow through the conductance cell and to optimize DC biasing of the multiplexer.

BRIEF DESCRIPTION OF THE DRAWINGS

The invention will be better understood if reference is made to the accompanying drawings, in which:

FIGS. 6 and 7 show timing diagrams illustrating the operation of the circuit.

DESCRIPTION OF THE PREFERRED EMBODIMENT

As indicated above, the inventions disclosed and claimed herein were made in connection with improvement of the instruments for the measurement of the total organic carbon content of water described in the five U.S. patents issued to the assignee of the present application listed above, and of the conductivity measuring circuits therefor disclosed and claimed in the three further U.S. patents also assigned to the assignee and referred to above. However, while the present invention is described as applied to that environment, it is to be appreciated that numerous teachings of the invention have applicability to other highly sensitive instruments, particularly where the electrical characteristics of a solution are to be monitored while the solution is exposed to radiation of a predetermined wavelength. Such applications may include instruments for measurement of oxidation during flow injection analysis, analysis of organic digestion or of nitrogen-containing-compound digestion, or other elemental analysis, or liquid chromatography detection, e.g., where ionized organic compounds in solution are measured by monitoring the conductivity of the solution. Many of the advantages provided by the present invention in connection with measurement of organic materials in water will be applicable to such additional applications, as well as others not mentioned. Further, the circuit described herein may be useful in a wide variety of applications wherein measurements of a particular electrical characteristic of a given device are to be calibrated by comparison to a reference device exhibiting a known value of the predetermined characteristic. Therefore, while the invention is described herein in detail in connection with a complete system for measurement of the total organic carbon content of water, the invention is not so limited.

Figure 1:
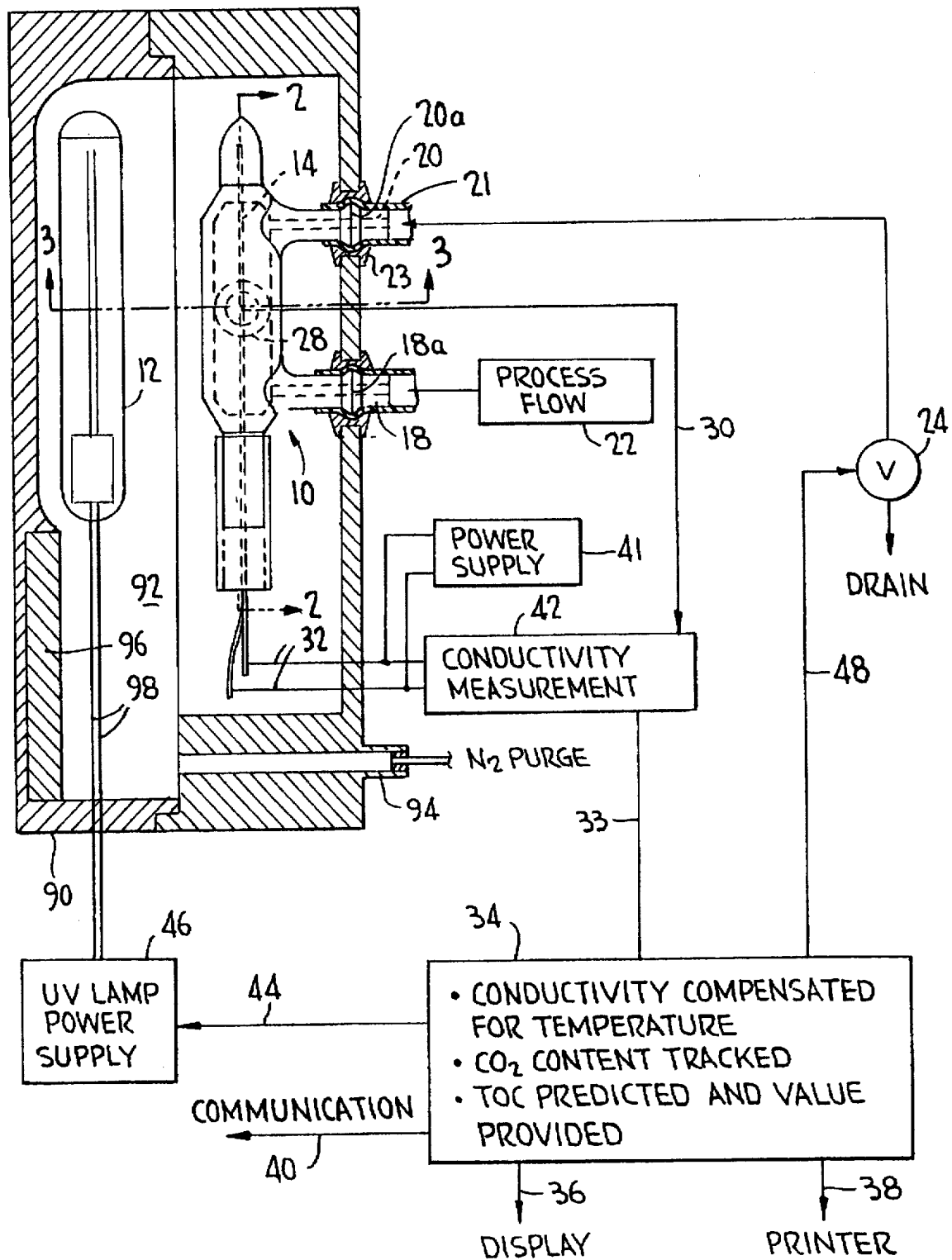
FIG. 1 shows schematically a system according to the invention as implemented for measurement of the total organic carbon content of water.
Figure 2:
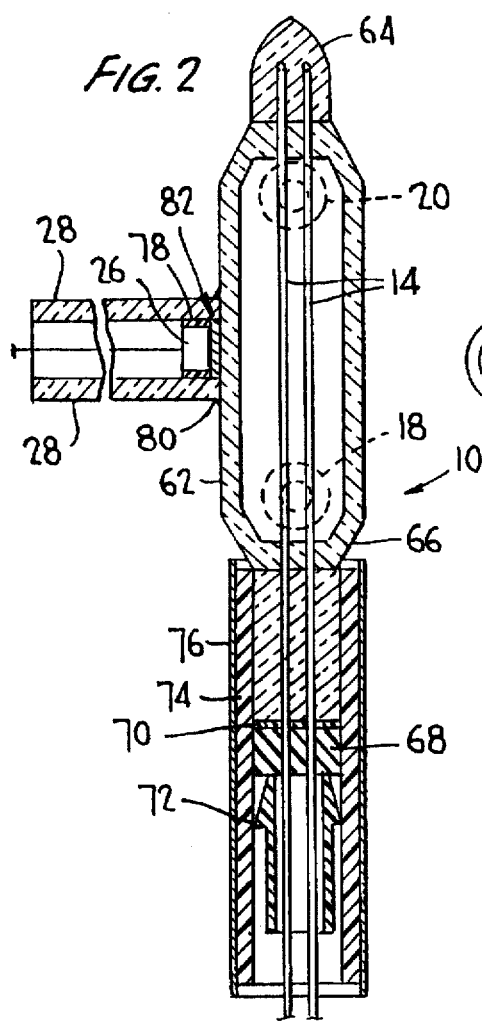
FIGS. 2 and 3 show cross-sections along the lines 2—2 and 3—3 of FIG. 1, respectively.
Figure 3:
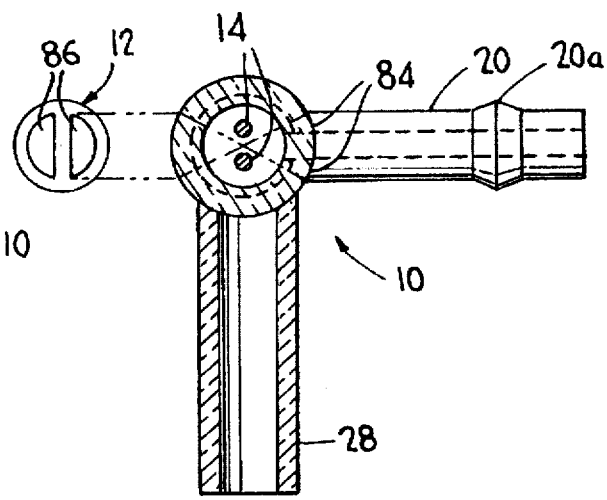

FIGS. 1–3 depict the physical cell according to the invention, together with its connections to the other principal components of a complete instrument.

A liquid sample to be analyzed is confined in a cell 10 while being exposed to radiation from a lamp 12. The electrical characteristics of the sample of interest are measured across a pair of electrodes 14 extending axially within the cell 10, parallel to the direction of elongation of the lamp 12; in particular, where the surfaces of the electrodes are of a material which catalyzes or stimulates a reaction of interest in the liquid when irradiated by the lamp, the electrodes 14 are arranged such that the plane in which they lie is perpendicular to a line connecting the lamp to the center of the cell. See FIG. 3. In this way, a substantial fraction of the surface area of the electrodes 14 is directly exposed to radiation from the lamp 12. The electrodes are spaced closely together to optimize their electrical response to conductivity changes.

Conveniently, the cell 10 is provided with an inlet tube 18 and an outlet tube 20; at minimum, at least one port in fluid communication with the internal volume of the cell must be provided, through which the liquid can be injected and later withdrawn, after the reaction has been completed.

In the case of oxidation of organics in a water sample to $CO_2$, water from a process source or the like, indicated generally at 22, is admitted to the cell by way of inlet tube 18, and is confined therein during the reaction; the sample's confinement is controlled by a valve 24 connected to the outlet tube 20. It is also within the invention to use the cell 10 in a continuous flow process. In either case, oxidation of the organics to $CO_2$ is driven by ultraviolet radiation from lamp 12, preferably including substantial components at 253 and 184 nm wavelength. The surfaces of the electrodes are preferably an N-type semiconductor catalyzing the oxidation; conveniently, these surfaces are $TiO_2$ formed by the oxidation of the surfaces of solid Ti electrodes 14. Other suitable materials include $SrTiO_3$, $CdS$, $WO_3$, $Fe_2O_3$, and $MO_3$. See commonly-assigned U.S. Pat. No. 4,868,127 (incorporated herein by reference) for a thorough discussion of the photocatalytic oxidation process.

Analysis of the reaction of organics to $CO_2$ in order to determine the total organic carbon ("TOC") of a water sample is carried out by measuring the conductivity of the water. The relation of $CO_2$ content to conductivity varies substantially with the temperature of the water. Accordingly, a temperature sensing device, typically a thermistor 26 (see FIG. 2) is secured at the base of a temperature sensor well 28 secured to one wall of the cell 10 such that the temperature sensor 26 is in good thermal contact with water in the internal volume of the cell 10. The varying resistance signal responsive to temperature provided by sensor 26 is supplied over conductor 30, together with the conductivity signal carried by conductor 32, to a conductivity measurement circuit 42. These signals are multiplexed prior to supply via conductor 33 to a control device 34, typically comprising a microprocessor, wherein the $CO_2$ content of the sample is converted to a value for the TOC of the sample. As indicated, typical output devices may include a visible display 36, a printer 38, or means for communication to a remote location or the like as indicated at 40.

Techniques whereby the TOC content of the sample is determined responsive to monitoring of the conductivity of the sample as a function of time are discussed in detail in the commonly-assigned patents referred to above, notably the most recent U.S. Pat. No. 5,275,957 (incorporated herein by reference), disclosing that desirably the conductivity measurements are converted to values for $CO_2$ content after temperature correction. Further, a series of $CO_2$ values may be used to predict the final $CO_2$ content of a given sample, where the values measured conform generally to previously-measured samples. Alternatively, in a particularly preferred analysis technique, the sample may be oxidized for a fixed period of time, and the conductivity measured thereafter, plural measurements being made to ensure that oxidation has been completed.

As indicated in FIG. 1, the signal on electrodes 14 is processed in a conductivity measuring circuit 42 discussed in detail below in connection with FIGS. 4–7 before being supplied to the controller 34. The controller 34 controls all aspects of the process, including operation of the UV lamp, as indicated by a control signal 44 supplied by the controller 34 to a UV lamp power supply 46, and operation of the drain valve 24, as indicated by signal connection 48.

Turning now more specifically to details of the construction of the cell, as indicated above, a primary object of the invention was to provide an inexpensive cell suitable for making high precision measurements of conductivity of small samples of very high resistivity, such that very sensitive measurements are essential. The overall reaction time is reduced depending on the intensity of the UV; accordingly, a cell efficiently collecting UV is desired. As a further constraint, it will be recognized by those of skill in the art that the use of short wavelength ultraviolet radiation to oxidize organics in a water sample means that the highly destructive ultraviolet radiation must be shielded from various UV-sensitive components, such as plastic or elastomer seals as might otherwise be used to form the cell. Further, it will be appreciated that in order to provide a low cost cell it is desirable to avoid significant amounts of machining of expensive materials; for example, in the commonly-assigned patents referred to above, the electrodes were machined, such that substantial amounts of titanium were reduced to scrap. Accordingly, the low-cost cell of the invention uses stock products assembled such that minimal machining and other costly operations are required. The cell shown in FIGS. 1–3 has many features which contribute to satisfaction of this goal.

Specifically, the cell 10 as shown in FIGS. 2 and 3 comprises an elongated main tube section 62 including at least a window formed of a material which is transparent to the radiation of interest; where the instrument is to be used for oxidation of organics in water to $CO_2$, the main tube is formed of a synthetic fused silica or fused quartz material transmitting 185 and 254 nm UV. In a presently preferred embodiment, a "Supracil" fused quartz tube 5 millimeters inside diameter ("ID"), 7 millimeters outside diameter ("OD"), and 0.75 inches long is used, such that a total internal volume of about 0.4 ml is provided. The electrodes 14 are two 0.75 mm diameter solid titanium rods cut to length and allowed to oxidize in water while exposed to UV, such that a $TiO_2$ surface layer is formed without other complicated steps, and without machining. To mount the two Ti electrodes 14, two sections of twinbore tubing 4.25 mm OD and having two parallel 0.82 mm bores therein are used, forming proximal end member 64 and distal end member 66 receiving the Ti electrodes 14. The electrodes are thus held parallel at a spacing of one mm. This close spacing ensures the conductance is significant even when the water being sampled is of low conductivity, extending the useful range of the instrument.

The twinbore tubing sections are formed of a material fusible to the fused quartz of the main tube 62 by conventional glass-blowing techniques; cerium-doped quartz is suitable for this purpose, and provides the further advantage of UV absorption. As indicated, the distal end member 64 is sealed off, while the electrodes 14 protrude from the proximal end member 66 so that electrical connections can be made thereto. The seal between the electrodes 14 and the proximal end member 66 may comprise a mechanical seal, an adhesive, or a glass/metal seal. Appropriate metals for a glass/metal seal, if used, include zirconium, tungsten, titanium, molybdenum, platinum, and tantalum. Of course, various materials may be used for electrodes 14, depending on the specific reaction to be measured in the cell 10. Catalytic members separate from the electrodes may also be employed.

In a successfully tested embodiment of the instrument of the invention as implemented for TOC measurement of high purity water samples, an elastomer septum 68 faced with a Teflon or other fluoroplastic layer 70, and having two apertures therethrough, is placed over the electrodes 14 and compressed firmly against the outer end of the proximal end member 66 by a mechanical locking device 72. Mechanical locking device 72 may comprise a molded barbed member, fitting into a fluoroplastic tube 74; tube 74 in turn is covered with a cylindrical foil 76 of a UV-resistant metal or the like, such that the fluoroplastic tube 74 is not attacked by the UV from source 12. The net result is that the sealing of the electrodes 14 to the cell 10 is accomplished readily, without exotic techniques.

As indicated above, temperature sensor 26 must be in thermal contact with liquid contained in the interior volume of cell 10 in order that accurate temperature measurements can be made and used to compensate measurements of the conductivity. To this end, a temperature sensor 26 having a resistance varying with temperature, typically a thermistor, is bonded in thermal contact with the wall of the cell 10 by a thermally conductive epoxy material 78. The thermistor is secured within a temperature sensor well 28 formed of a further UV-absorptive cerium-doped quartz tubing 3 mm ID by 5 mm OD such as that sold as Heraeus M382. As indicated, the well 28 is fused to the outside surface of the main tube 62 at bonding lines 80; the main tube 62 is not perforated at this location. More particularly, the wall thickness of the main tube 62 is preferably unaffected in the process of securing the temperature sensor well thereto, such that temperature measurements are repeatable from one cell to the next. In order to protect the thermistor or other temperature sensor from UV, a shield 82 of thermally conductive, UV-reflective metal or the like is placed in the bottom of the well. This metal may be copper, aluminum, or gold.

Inlet and outlet tubes 18 and 20, respectively, are also provided. These may be formed of 1 mm ID by 3 mm OD Heraeus M382 or GE254 type quartz tubing, and fused to the main tube along lines 84; of course, the wall of the main tube 62 is perforated at those locations to enable a fluid sample to enter and exit the internal volume of the cell 10. The inlet and outlet tubes 18 and 20 are formed with sharp-edged circumferential ridges (referred to as 'olives' in the art) 18a and 20a, so as to form a reliable seal to elastomeric connecting tubes 21; tubes 21 can then be sealed to housing 90 by a UV-resistant epoxy, or a low melting temperature alloy, such as an indium- or bismuth-based solder, as indicated at 23. Provision of the elastomeric tubes 21 allows differential thermal expansion of the cell and housing without breakage.

The relationship of the lamp 12 providing UV radiation to the interior volume of the cell 10 is shown schematically in FIG. 3. A typical low pressure mercury vapor lamp emits UV in the 184 and 254 nm wavelength ranges most efficient in the destruction of organics (more specifically, emitting effective amounts of radiation at 184.9 nm and 253.6 nm). It is desirable to space the lamp from the cell by a distance approximately equal to the diameter of the cell, such that radiation from the lamp 12 tends to be concentrated in the center of the internal volume of the cell 10. Of course, additional focusing means could also be provided, but would add to the expense of the cell. If further increases in the reaction rate are desired, many reactions (including the oxidation of organics in water) may be accelerated by application of DC power, e.g., across electrodes 14, from a power supply 41. In a preferred embodiment, the lamp is a model 71-9025-01 provided by BHK Corporation of Pomona, Calif., and is disposed approximately 5 mm from the outer surface of the cell 10, which is 7 mm OD, as mentioned above. Obviously other radiation sources may require differing arrangements to ensure efficient photochemical reactions within the sample volume defined by the cell 10. Members 86 shown in FIG. 3 depict "D"-shaped channels containing the mercury arc of a typical low-pressure mercury vapor lamp.

As is well known, ultraviolet radiation is absorbed by oxygen and ozone in the air. More specifically, oxygen is converted to ozone by 184 nm UV, and 253 nm UV is absorbed by ozone. To keep the instrument efficiency high, it is desirable to seal the UV lamp 12 within a container and prevent absorption of the UV by oxygen or ozone. According to this aspect of the invention, the lamp and cell are mounted in a single housing 90 defining a sealed chamber 92. If oxygen is removed from the chamber 92, e.g., by introduction of nitrogen through a purge port 94, absorption of the UV by oxygen is substantially precluded. However, for some users this may be inconvenient, for example, if lamp changes are required, or if the seals leak air. Therefore, according to a preferred embodiment of the invention, a quantity 96 of oxygen and/or ozone absorptive material is also placed in the chamber 92. This may comprise, for example, a quantity of activated charcoal confined in a fiberglass sheath, or a quantity of finely divided aluminum wire; oxidation of the carbon to $CO_2$, or the aluminum wire to $Al_2O_3$, both reactions being effective in the presence of ozone, consumes the oxygen and ozone in the chamber 92.

Finally, it will be appreciated by those of skill in the art that the preferred orientation of the cell 10 is as shown in FIG. 1, that is, with the outlet 20 vertically above the inlet 18; this prevents bubble formation within the internal volume of the cell 10. Lamp 12 is preferably oriented oppositely than shown in FIG. 1, i.e., with the power connections 98 above the lamp 12 itself; this limits convection in the chamber 92. The orientation shown in FIG. 1 is more convenient in diagramming the various connections.

Figure 4:
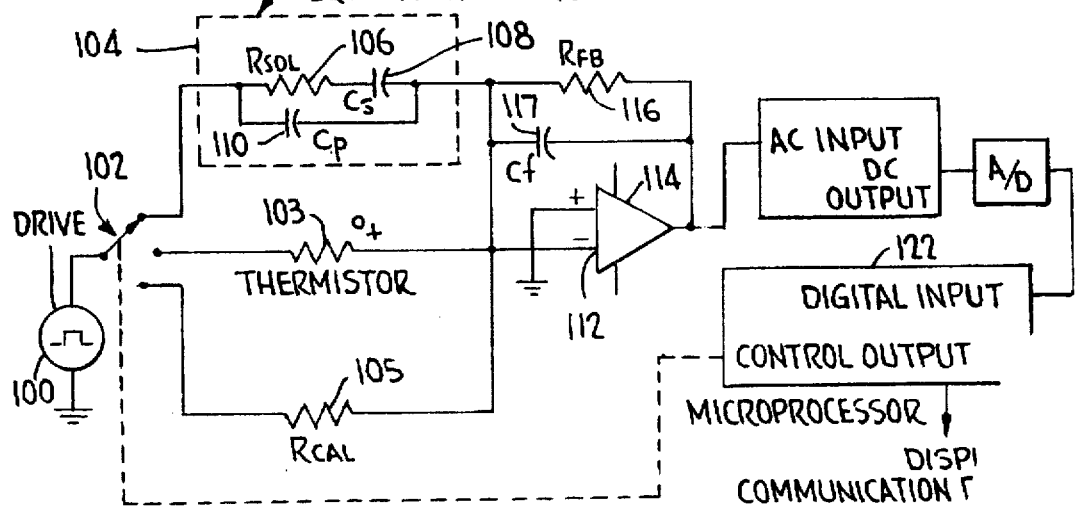
FIG. 4 shows a block diagram of the conductivity measuring circuit.
Figure 5:
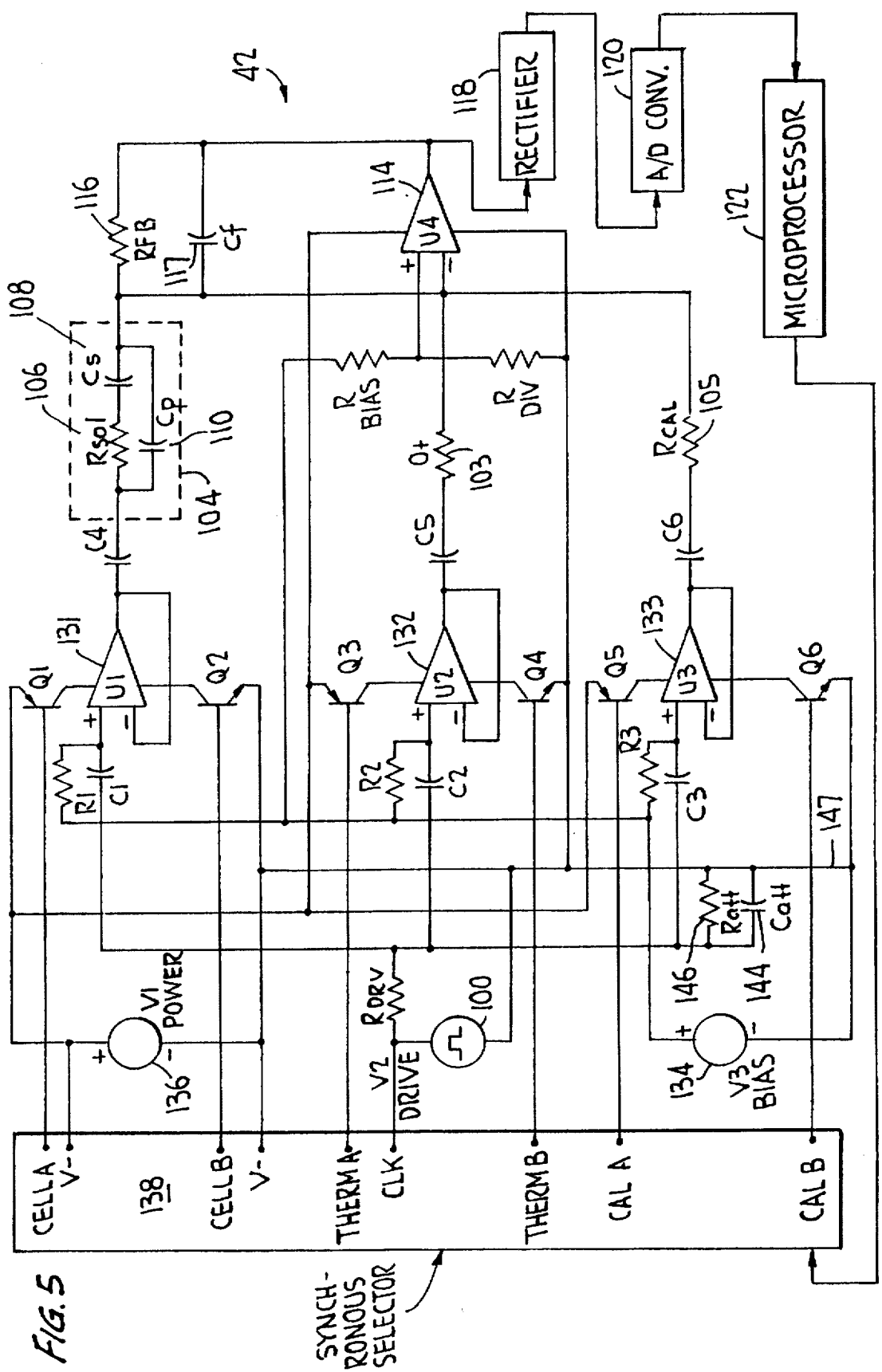
FIG. 5 shows a more detailed circuit diagram of the analog portion of the conductivity measuring circuit.

FIG. 4 shows a block diagram of the conductivity-measuring circuitry 42 of the instrument, FIG. 5 shows a more detailed circuit diagram of the conductivity-measuring circuit 42 and its connection to additional system components, and FIGS. 6 and 7 show diagrams illustrating the various control and conductivity signals as functions of time; FIG. 7 is effectively an enlargement of one portion of FIG. 6.

As stated above, operation of the circuit (in an implementation optimized for measuring the conductivity of water during UV radiation) comprises repetitively multiplexing a common AC input signal to a calibration resistor, a thermistor, and the sample cell, and analyzing their respective responses thereto. Preferably, the system response is also monitored during a period while the input signal is not applied to a load; this allows a system offset (i.e., calibration at zero conductivity) value to be measured. The AC current through each resistive load is first converted to an AC voltage, then rectified to a DC voltage, and then converted to a digital value; in the preferred embodiment, digitization is performed by converting the voltage to a variable-frequency signal and then counting the number of zero-crossings in a fixed sample time to determine the amplitude of the voltage.

More specifically, the corrected cell conductance is calculated ratiometrically by dividing the "calibration frequency", i.e., the frequency measured responsive to the conductance of the calibration resistor minus the "offset frequency", by the difference between the "conductance frequency" of the cell and the "offset frequency", responsive to the current flowing through the measurement circuit with the three principal loads mentioned all disconnected. The offset thus compensates for any DC errors in the measurement circuit.

Referring now to the block diagram of FIG. 4, a square wave drive signal is applied from a source 100 to a multiplexing switch 102, the detailed structure of which is shown in detail in FIG. 5. Switch 102 applies the drive signal in succession to a group of loads, in this implementation including the cell 104, a thermistor 103, and a calibration resistor 105. An equivalent circuit corresponding to the conductivity cell 104 comprises a series resistance $R_{sol}$ 106, a series capacitance $C_s$ 108, and a parallel capacitance $C_p$ 110. The sources of and approximate values for each are discussed in detail in commonly assigned U.S. Pat. Nos. 5,260,663 and 5,334,940 referred to above, and incorporated herein by this reference. Those of skill in the art will recognize that the cell of FIGS. 1-3 exhibits a higher cell constant that those of the commonly-assigned patents referred to above, and therefore a higher value for the resistance $R_{sol}$ for a given sample, and correspondingly lower relative values of $C_p$ and $C_s$.

The outputs of the multiplexed loads are applied to the inverting input 112 of an operational amplifier U4 114 configured as a transimpedance amplifier, with a feedback resistance $R_{fb}$ 116 and feedback capacitance $C_f$ 117. The AC output signal from op-amp 114 is supplied to a rectifier 118 converting the AC signal to a DC voltage; this in turn is supplied to an analog-to-digital converter 120 providing a digital output to microprocessor 122 calculating the TOC content generally as discussed above and in connection with the teachings of the commonly-assigned patents referred to above and incorporated herein by reference.

More specifically, and as discussed generally above, according to one aspect of the invention, the drive signal from source 100 is applied successively to input terminals of the conductivity cell 104, the thermistor 103 or other temperature sensor, and a calibration resistor 105, as shown by the logic-level signals of FIGS. 6(a)–(c), respectively, and corresponding to the 'SYSTEM CYCLE' status line above FIG. 6(a). The current passing through each load is measured by operational amplifier ("op-amp") 114 configured as a transimpedance receiver converting this current into a voltage. Experimentation with this circuit showed that each input should be periodically switched on to avoid errors. Accordingly, each of the inputs is sampled repetitively in a regular pattern shown in the timing diagram of FIG. 6. This pattern is configured such that the most sensitive input, that is, the cell, which is of extremely low conductivity when containing samples of the lowest conductance (up to 18 MΩ-cm), is addressed for the longest period of time in order to increase overall accuracy. An overall system time cycle is divided into ten equal blocks of 71.11 ms, and the input drive signal is applied to the loads as follows: seven blocks (I–VII) to the cell (FIG. 6(a)), one block (VIII) to the temperature sensor (FIG. 6(b)), and one block (IX) to the calibration resistor measurement (FIG. 6(c)). During a tenth "offset" block (X), the input drive signal is not connected to any of the loads; during this period, the system offset value, i.e., any DC background current flowing at zero conductivity, is measured for use in compensating the measurements of the conductivity of the loads.

The DC conductivity signal provided at the output of rectifier 118 is shown in FIG. 6(d). Capacitance throughout the circuit causes the DC conductivity signal to change exponentially to its stable value upon each change of system status, i.e., as the drive signal is applied to each load in succession. Therefore, the conductivity of each load is measured only during sample times indicated by crosshatching in FIG. 6(d).

All conductivity measurements are performed commencing after the input signal has had a chance to settle, that is, during the cross-hatched sample times shown in FIG. 6(d), each about 60 ms in duration, and commencing approximately ten milliseconds after the switching point and ending approximately 1 ms before commencement of power application to the next load. Measurement of the conductivity of the cell takes place only in the last of the seven blocks during which the drive signal is connected to the conductivity cell. The conductivity signal is also measured during an offset sample time, in block X, during which all of the op-amps are off. In the preferred embodiment, microprocessor 122 is used to control switching and timing, but other methods could be employed as well.

Turning now to FIG. 5, significant components of the conductivity measurement circuit 42 of FIG. 1, and in particular the input multiplexing switch 102 of FIG. 4, comprise op-amp 131 connected in series with the conductivity cell 104, op-amp 132 in series with the thermistor 103, and op-amp 133 in series with the calibration resistor 105. The non-inverting inputs of each of the op-amps 131, 132, 133 are connected to the source 100 of the square wave drive signal, but each op-amp conducts the drive signal to its associated load only when supplied with power from source 136. Op-amps sold as Model No. TL081 by Texas Instruments, Dallas, Texas are suitable for these components. Source 136 is connected to the op-amps 131, 132, 133 by positive-side switching transistors Q1, Q3, and Q5, and negative (return)-side switching transistors Q2, Q4, and Q6 connect the op-amp return terminals to ground. The transistor pair Q1, Q2 controlling power supply to op-amp 131, and thus controlling flow of the drive signal through conductivity cell 104 is controlled by CELL A and CELL B signals provided by a synchronous selector unit 138 controlled by the microprocessor 122. Similarly, flow of the drive signal through the thermistor is controlled by supply of power to op-amp 132, responsive to control signals THERM A and THERM B connected to the bases of Q3 and Q4; similarly, signals CAL A and CAL B are supplied to the bases of Q5 and Q6, to control conduction of the square wave drive signal through op-amp 133 in series with calibration resistor 105. The timing diagram of FIG. 6 illustrates the sequence of the control signals CELL B, THERM B, and CAL B, (CELL A, THERM A, and CAL A being their inverses, and not shown) and thus illustrates the sequence whereby the drive signal provided by source 100 is multiplexed between the conductivity cell, the thermistor, and the calibration resistor, respectively.

Coupling capacitor pairs C1, C4, C2, C5, and C3, C6 on the input and output sides of the op-amps 131, 132, and 133 respectively decouple the op-amps and eliminate any DC bias in the drive signal that might arise over time due to aging of the components and the like. The output coupling capacitors C4, C5, C6 also eliminate DC errors due to cell polarization, in short, eliminate all DC differences between the input channels. Provision of C4 in particular compensates for a DC voltage induced on the electrodes due to "photoelectric effects" caused by irradiation of the electrodes with UV. The time constant of C4 in series with the solution resistance $R_{sol}$ is selected to be much shorter than that of the photoelectric effects, which is typically on the order of several minutes.

Prior art practices typically required such output coupling capacitors to be rather large and expensive to keep the series impedance small in relation to the measured conductivity. According to one aspect of the invention, the DC error due to the charging of the output capacitors is allowed to reach two percent, and is then compensated by a quadratic approximation to the exponential function whereby the measured conductivity is converted by the microprocessor to values for $CO_2$ content of the sample. The coefficient for the coupling capacitor correction is determined by an automatic single point calibration of maximum conductivity performed at manufacture.

Each output coupling capacitor retains a specific charge and voltage when the corresponding input is turned off. Because this charge is different on negative and positive half cycles, commencement of the application of the input drive signal to a new load (FIGS. 6(a)–(c), FIG. 7(e) and (f)) is synchronized to the conductivity DRIVE signal (FIG. 7(c)). The switching of the input from one load to the next is separated in time from either edge of the conductivity DRIVE signal to allow for settling of the switching transients. The middle of the positive DRIVE half cycle (see FIG. 7(c)) was found empirically to be the most practical input switching time (see FIG. 7(d)). Switching the inputs in a consistent timing cycle ensures consistent measurements; otherwise, leakage from the op-amp input and output terminals to the power terminals while turned off introduces an error responsive to the amount of time that the input is turned off.

More specifically, FIGS. 7(a)–(g) show timing diagrams which expand the region between the blocks VII and VIII of FIG. 6, as an example of the timing of the entire circuit. The CELL B and THERM B signals of FIGS. 7(e) and (f), respectively, correspond to those in FIGS. 6(a) and (b). FIG. 7(a) shows a SAMPLE signal used to control the sampling of the conductivity signal during the cross-hatched sampling periods shown in FIG. 6(d); the conductivity of the load then connected to the input signal is sampled at the intervals shown, that is, once per each cycle of the DRIVE signal. FIG. 7(b) shows a double-speed CLOCK signal used to clock the sampling of the conductivity of the load, as indicated by the SAMPLE signal of FIG. 7(a), as well as switching of the load to which the DRIVE signal is connected, illustrated by comparison of FIGS. 7(e) and (f). As indicated, the period of the double-speed CLOCK is half that of the DRIVE signal shown in FIG. 7(c), such that the double-speed CLOCK provides a transition in the center of each half of DRIVE; the SAMPLE signal is triggered by this transition, which is also used to control switching of the input signal from one load to the next in sequence. Compare FIGS. 7(e) and (f).

As explained in commonly-assigned U.S. Pat. Nos. 5,260,663 and 5,334,940, a parallel capacitance $C_p$ in the cell equivalent circuit (as well as any stray capacitance in the measurement circuit) causes the AC conductivity signal (FIG. 7(g)) to vary exponentially upon each half-cycle of application of DRIVE to the cell. For this reason, the conductivity of the cell is sampled during a sample time toward the end of the application of DRIVE to the cell. The conductivity of the other loads does not vary in this fashion, but for simplicity's sake their conductivities are measured similarly. Sampling the conductivity of the loads during the latter half of the positive half-cycle of DRIVE, as shown, ensures that the exponentially-decaying peak in the AC conductivity signal (FIG. 7(g)) due to $C_p$ charging will have reached a stable level when the conductivity is measured. As indicated, the same technique is disclosed in the commonly-assigned patents referred to above.

More specifically, the system block status determines the load as to which the conductivity is measured and is controlled by microprocessor 122. As indicated by FIG. 7, the transition between blocks typically occurs at a time which does not correspond to a transition of the DRIVE signal, such that the microprocessor need not be synchronized to DRIVE. Accordingly, a delay of up to on the order of one millisecond occurs between the end of each block and the center of the next negative half-cycle of the DRIVE signal, at which time DRIVE is then applied to the successive load. This is illustrated by the transition between the CELL B signal (FIG. 7(e)), controlling application of the DRIVE signal to the conductivity cell, and the THERM B signal (FIG. 7(f)) controlling application of the DRIVE signal to the thermistor. Stated slightly differently, after the microprocessor has timed out the end of a particular block, e.g., block VII in the example, the DRIVE signal is then applied to the next load in sequence at the transition of the double-speed CLOCK signal occurring in the middle of the next negative half of the DRIVE signal, as shown. Accordingly, a delay of up to one ms is shown between the end of each block and the switching of the DRIVE signal in FIG. 6. Consistently switching the DRIVE signal at the same point in corresponding cycles allows charge on coupling capacitors C1–C6 to be maintained constant.

The finite impedance of the measured resistivities causes charge to be stored by the output drive capacitor during the positive drive cycle, and subtracted during the negative drive cycle, while any of the channels is turned on. Charge is stored at a rate dependent on the drive voltage, capacitor value, and resistivity being measured. To maintain equilibrium of charge in each capacitor, the op-amp of that particular channel must be turned on at the same relative point in the drive cycle at which it was turned off. Accordingly, as discussed above, the op-amps are turned on and off in the middle of the negative half-cycle of the drive signal, such that the negative and positive charges stored are equal.

In the preferred embodiment, analog-to-digital conversion is performed by first converting the AC output current to a voltage, rectifying this to a DC voltage, converting this voltage to a frequency, and then using a timer to measure the frequency and thus digitize the output of the circuit, this being performed with respect to each of the conductivity cell, thermistor, and calibration resistor output signals, so that the microprocessor can conveniently analyze the results. The current-to-voltage conversion is implemented by a further op-amp 114, provided with parallel-connected feedback resistance $R_{fb}$ 116 and capacitance $C_f$ 117, so as to operate in transimpedance configuration. A similar conversion technique is employed in the circuits of U.S. Pat. Nos. 5,260,663 and 5,334,940, preferred to above; however, the range-setting feedback resistor network 24 employed therein is eliminated from the present circuit, for reasons of cost.

The voltage-to-frequency conversion technique described was chosen over dual-slope integrating or successive approximation analog-to-digital converters to save cost. Because a voltage-to-frequency converter cannot express a zero or negative frequency, the input must always be positive. Accordingly, a DC offset is deliberately introduced into the measurement by way of bias source 134 and resistors R1, R2, R3, $R_{bias}$, $R_{div}$ (see FIG. 5). The offset is compensated for by measurement during the offset period (see FIG. 6(d)) during which none of the other inputs are on. Similarly, the synchronous rectifier or voltage-to-frequency converter may exhibit bi-polar offset, e.g., due to production tolerances or temperature variation. By measuring the actual offset during the off period, and subtracting the offset value from the cell, thermistor, and calibration resistance measurements, these measurements are compensated for any inaccuracy.

It can thus be seen that according to this aspect of the invention, the three op-amps 131, 132, 133 are employed as switches. These replace prior art switching techniques using either relays or field effect transistors in the AC signal path. The primary advantage of employing op-amps in this circuit is to eliminate the substantial cost of relays or field effect transistors suitable for handling the very low currents experienced in TOC measurement, on the order of 800 na. Specifically, dry contact relays are unreliable at current levels below 10 microamperes, and are thus unsuitable for TOC measurements in water. FET-based silicon multiplexers have significant resistance and leakage currents that limit conductivity measurement and dynamic range. Mercury switches are electrically satisfactory but mechanically complex.

Having described the operation of the circuit in detail, certain comparisons with the prior art as represented by commonly-assigned U.S. Pat. Nos. 5,260,663 and 5,334,940 can now be made. As described in detail in those patents, a conductivity cell, especially as used to contain a sample of water during exposure to UV, exhibits a series capacitance $C_s$ and a parallel capacitance $C_p$. While the techniques described in those patents to eliminate the effects of $C_p$ and $C_s$ on measurement of the conductivity of the cell are very effective, the circuitry involved is rather costly; according to the present invention, a much less expensive circuit is provided, at only slight sacrifice in dynamic range.

The desired precision is attained by three principal circuit techniques. First, an attenuating capacitor $C_{att}$ 144 (FIG. 5) is provided, connected between the drive signal source 100 and the return to ground 147, in parallel with an attenuating resistor $R_{att}$ 146. The ratio between $R_{dry}$ 148, connected between the drive signal source 100 and the noninverting inputs of each op-amp, and $R_{att}$ 146, connected between the noninverting inputs and return 147, provides a voltage divider effectively limiting the amplitude of the input signal. In this way, the input signal does not become powerful enough to turn on the op-amps, except when power is applied thereto. More specifically, as will be appreciated by those of skill in the art, op-amps generally comprise a large number of diodes and transistors; if the input signal exceeds about one volt peak-to-peak, the internal diodes may conduct the drive signal, which would interfere with the measurements being made by other parts of the circuit. Providing $R_{att}$ as shown limits the input signal accordingly.

Providing $C_{att}$ attenuates the high frequency components of the square-wave DRIVE signal, assuring that the maximum rate of change of the drive signal at the input terminals of the op-amps does not exceed their ability to follow their respective input signals. This allows the op-amps to function in closed-loop feedback mode. Furthermore, the error signal caused by $C_p$ consists of high frequencies from the drive waveform, which are differentiated by $C_p$. With only the attenuated high frequencies driving the cell, the error introduced by $C_p$ is also attenuated.

The second principal technique used to reduce the $C_p$ error is providing feedback capacitor $C_f$ 117 across the transimpedance amplifier 114. Essentially, the circuit shown forms an AC inverting amplifier with gain equal to $-C_p/C_f$. $C_f$ is chosen to be three or more times $C_p$, attenuating $C_p$ error accordingly.

The third technique for reducing $C_p$ error is essentially the same as shown in the two commonly-assigned patents, that is, only sampling the conductivity of the cell at a time when the error due to $C_p$ has been reduced by $C_p$ having been fully charged. As shown by FIGS. 7(a) and (g), the conductivity of the cell is measured at intervals defined by SAMPLE, each during the latter half of each half-cycle of DRIVE, so that the conductivity is measured only after $C_p$ is fully charged.

Furthermore, sampling only takes place during the crosshatched cell sample times (FIG. 6(d)), towards the end of the period of application of the drive signal applied to the each load. This provides time for any switching transients or the like to settle out, and also allows time for charging various capacitances external to the cell, which round off the DC conductivity signal as shown at 150 (FIG. 6(d).

The $C_s$ error is controlled by using a drive signal frequency (typically 1 Khz) sufficient to ensure that the error is acceptable over the range of measured conductances addressed by this particular circuit, and can be reduced by a simple mathematical correction applied by the microprocessor, recognizing that $C_s$ varies with the conductance of the solution.

The commonly-assigned patents mentioned above use a switched resistor network to provide range switching. Range switching is not provided according to the circuit of the invention as shown, but could be implemented in the same way; alternately the drive frequency or the drive level could be changed, e.g., by varying the value of $R_{att}$ 146.

In the commonly-assigned patents mentioned above, the drive signal is synchronized to the lamp power supply signal, so that the substantial high-frequency noise due to the lamp signal would average out. It was desired to avoid such synchronization in the present circuit. Accordingly, the lamp is simply turned off at the times conductivity measurements are to be made. This eliminates the noise due to the lamp drive signal. Typically, after a new sample of water is introduced into the cell, a background conductivity measurement is made. The lamp will be powered continuously for 90-120 seconds after which the lamp will be turned off for about one second to allow a conductivity measurement to be made; the lamp may then be energized again for 5 to 10 seconds, followed by a second conductivity measurement. If the two measurements are the same, the organics in the sample have been oxidized completely, and a value for the TOC of the sample can be output by comparison of the background and final conductivity values. If there is some variation, the oxidation process may continue for some time.

While this method of operation does not permit the conductivity to be tracked continuously, as in the commonly-assigned patents referred to above, it is found in practice that the lamp and cell design shown are sufficiently efficient that practically all organics of interest are fully oxidized in the period of 90-120 seconds. Alternatively, of course, the drive signal could be synchronized to the lamp frequency as in the patents referred to above, or measurements could be taken at fixed lamp-off intervals, although at some cost in lamp life due to the necessity of repetitively turning the lamp on and off. Tests to date indicate that turning the lamp off for several one-second measurements every five seconds or so at overall intervals of several minutes does not allow the lamp to cool to the degree that lamp life becomes a problem.

As indicated above, the TOC value thus determined may be displayed for operator use, employed as a control input in management of a processing system, such as a high purity water supply sytem, or otherwise.

While the requirements of high dynamic range and accuracy at very low conductivity levels are perhaps most significant in connection with TOC measurement in ultrapure water, it will be appreciated by those of skill in the art that this circuit may have use in significantly different fields. For example, the circuit of the invention may be useful wherever inputs to an analog-to-digital converter must be multiplexed between an experimental device in which an electrical characteristic of a sample—such as its impedance, inductance, or resistance—is to be measured by comparison to another load, such as a calibration load, thermistor, or other multiplexed device, or where such a measurement is to be corrected by subtraction of a system offset value measured during a period when the drive signal is not applied to any load. Therefore, the invention should not be limited to measurements of conductivity in high purity water for evaluating the TOC thereof. Similarly, as mentioned above, the cell of the invention and the method of its use may be useful wherever a photochemical reaction is to be monitored by analysis of an electrical characteristic of the sample.

Therefore, while a preferred embodiment of the invention has been discussed in detail, the invention should not be limited thereby, but only by the claims which follow.

What is claimed is:

1. A cell for monitoring the electrical characteristics of a liquid during exposure to radiation, comprising:
    an elongated generally tubular member defining an elongated internal sample volume, said member comprising a tube of a fusible material transparent to said radiation selected from the group consisting of glass fused silica or fused quartz;
    at least one liquid port in fluid communication with said internal volume;
    first and second end members formed of a material fusible to the material of said tubular member, said end members being fused to said tubular member, delimiting ends of said sample volume;
    a pair of elongated continuous rod electrodes supported by said end members to be spaced from and parallel to one another along an axis of elongation of said tubular member, within said sample volume; wherein first ends of said electrodes are supported by said first end member, being sealed thereby within said internal volume, and second ends of said electrodes extend through and are sealed to said second end member, such that electrical conductors may be connected directly to said second ends of said electrodes for connection to external circuitry for monitoring the electrical characteristics of a livid in said internal volume during exposure to radiation.

2. In combination, the cell of claim 1, and an elongated source of radiation of predetermined wavelength, extending parallel to the axis of elongation of said tubular member, such that radiation from said source is incident on liquid in said internal volume.

3. The combination of claim 2, wherein said electrodes are oriented with respect to said source of radiation such that an effective fraction of a surface of both electrodes is directly exposed to radiation from said source.

4. The combination of claim 3, wherein the surface of said electrodes is formed of a material photocatalytically stimulating a reaction of interest in said liquid upon exposure to radiation of said predetermined wavelength from said source.

5. The combination of claim 4, wherein said reaction of interest is the oxidation of organic carbon-containing materials in ultrapure water to carbon dioxide, said radiation of predetermined wavelength includes ultraviolet radiation, and the material of the surface of said electrodes is an N-type semiconductor.

6. The combination of claim 5, wherein the N-type semiconductor material of the surface of said electrodes is selected from the group including $TiO_2$, $SrTiO_3$, $CdS$, $WO_3$, $Fe_2O_3$, and $MO_3$.

7. The combination of claim 6, wherein said semiconductor material is $TiO_2$, formed by oxidation of a surface of solid Ti electrode members.

8. The combination of claim 5, wherein said source of ultraviolet radiation is a mercury vapor lamp emitting radiation at substantially 184.9 and 253.7 nm wavelengths.

9. The combination of claim 8, wherein said source of ultraviolet radiation is disposed within a sealed chamber containing a quantity of an oxygen-absorptive substance.

10. The combination of claim 9, wherein said oxygen-absorptive substance is selected from the group consisting of activated charcoal and aluminum.

11. The combination of claim 5, further comprising a valve operatively connected to said port for defining a static sample of water to be exposed to said radiation.

12. The cell of claim 1, wherein said first and second end members are formed of sections of glass twinbore tubing fused to first and second ends of said generally tubular member, and said ends of said electrodes are received within first and second bores of said twinbore tubing.

13. The cell of claim 12, wherein said sections of glass twinbore tubing are formed of ultraviolet-absorptive glass.

14. The cell of claim 1, wherein said second ends of said electrodes extending through said second end member are sealed to said internal volume by an elastomer seal urged against said second end member by mechanical compression means external to said internal volume.

15. The cell of claim 1, wherein said at least one liquid inlet port in fluid communication with said internal volume comprises a glass tube fused to said generally tubular member, such that fluid communication is established therebetween.

16. The cell of claim 1, wherein first liquid inlet and second liquid outlet ports are provided, each comprising a glass tube fused to said generally tubular member, such that fluid communication is established therebetween.

17. The cell of claim 1, further comprising a temperature sensor well fused to said generally tubular member, said well receiving a temperature sensor for measuring the temperature of a liquid within said internal volume whereby measurements of electrical characteristics of said liquid may be accurately corrected in response to the temperature of said liquid.

18. The cell of claim 19, wherein a portion of said generally tubular member forming a bottom of said well is provided with a ultraviolet-absorbing, thermally conductive coating.

19. The cell of claim 18, wherein said ultraviolet-absorbing coating is selected from the group consisting of copper, aluminum, and gold.

20. A method of making a cell for containing a sample of liquid while simultaneously irradiating liquid therein with radiation of predetermined wavelength from a source and monitoring a predetermined electrical characteristic of the liquid, comprising the steps of:

providing an elongated first section of tubing formed of a glass, fused silica, or fused quartz material substantially transparent to said radiation of predetermined wavelength;

providing first and second end members of a material fusible to the material of said tubing in order to seal the ends of said first section of tubing, said end members comprising support means for supporting two parallel elongated electrodes extending, along the center of said first section of tubing;

providing two elongated electrodes of a material suitable for monitoring said predetermined electrical characteristic of said liquid during irradiation;

providing at least one tube of a material fusible to the material of said first section of tubing;

fusing said at least one tube to said first section of tubing such that a fluid communication path is established into an interior of said first section of tubing;

mounting said electrodes into said end members; and fusing said first and second end members to first and second ends of said first section of tubing, such that said electrodes extend parallel to one another axially along the interior of said first section of tubing, and such that first ends of the electrodes are sealed within said first end member and second ends of the electrodes extend out of the second end member.

21. The method of claim 20, comprising the further steps of providing a second tube of a material fusible to the material of said first section of tubing; and fusing said second tube to said first section of tubing, such that fluid inlet and outlet communication paths are established into the interior of said first section of tubing.

22. The method of claim 21, wherein said radiation of predetermined wavelength includes ultraviolet radiation, and wherein the material of said at least one inlet tube, said at least one outlet tube, and said end members is an ultraviolet-absorptive quartz.

23. The method of claim 20, comprising the further steps of providing at least one temperature sensor well tube of a material fusible to the material of said first section of tubing; and fusing said at least one temperature sensor well tube to said first section of tubing, such that said temperature sensor well is not in fluid communication with the interior of said first section of tubing.

24. The method of claim 23, wherein said radiation of predetermined wavelength includes ultraviolet radiation, and wherein the material of said at least one temperature sensor well tube is an ultraviolet-absorptive quartz.

25. The method of claim 24, comprising the step of placing a layer of ultraviolet-absorptive, thermally conductive material over a portion of said first section of tubing at a base of said temperature sensor well tube.

26. The method of claim 25, wherein said ultraviolet-absorptive, thermally conductive material is selected from the group consisting of copper, aluminum, and gold.

27. The method of claim 20, wherein said cell is intended for monitoring changes in conductivity of water containing organic carbon compounds during irradiation by radiation of predetermined wavelength including ultraviolet radiation, and comprising the step of selecting surfaces of said electrodes to comprise a material which catalyzes oxidation of said organic carbon compounds when exposed to said radiation.

28. The method of claim 27, wherein the material of the surface of said electrodes is an N-type semiconductor.

29. The method of claim 28, wherein the N-type semiconductor material of the surface of said electrodes is selected from the group consisting of $TiO_2$, $SrTiO_3$, CdS, $WO_3$, $Fe_2O_3$, and $MO_3$.

30. The method of claim 29, wherein said semiconductor material is $TiO_2$, and comprising the step of forming said $TiO_2$ on the surface of said electrodes by oxidation of the surface of solid Ti electrode members.

31. The method of claim 27, comprising the further step of mounting said cell in a housing, said housing comprising a lamp emitting radiation of predetermined wavelength including ultraviolet radiation.

32. The method of claim 31, wherein said lamp is a mercury vapor lamp emitting radiation at substantially 184.9 and 253.7 nm wavelengths.

33. The method of claim 32, comprising the further step of disposing said lamp within a sealed chamber including a quantity of an oxygen- and ozone-absorptive substance.

34. The method of claim 33, comprising the further step of selecting said oxygen- and ozone-absorptive substance selected from the group consisting of activated charcoal and aluminum.

35. The method of claim 20, wherein said first and second end members are formed of sections of glass twinbore tubing fused to the first and second ends of said first section of tubing, and said ends of said electrodes are received within first and second bores of said twinbore tubing.

36. The method of claim 35, wherein said sections of glass twinbore tubing are formed of ultraviolet-absorptive glass.

37. The method of claim 35, comprising the further step of sealing said second ends of said electrodes extending out of said cell to said first section of twinbore tubing by an elastomer seal urged thereagainst by mechanical compression means external to said internal volume.

38. The method of claim 37, wherein said mechanical compression means comprises a barbed tubular member fitting over said distal ends of said electrodes, and fitting within a plastic tube fitting over said first section of twinbore tubing.

39. The method of claim 38, comprising the further step of masking said plastic tube with a ultraviolet-resistant foil.

* * * * *